US012791539B2

(12) United States Patent
Shanai et al.

(10) Patent No.: US 12,791,539 B2
(45) Date of Patent: Nov. 10, 2026

(54) COMPOSITE MATERIAL PHYSICAL PROPERTY VALUE ESTIMATION DEVICE, COMPOSITE MATERIAL PHYSICAL PROPERTY VALUE ESTIMATION PROGRAM, AND COMPOSITE MATERIAL PHYSICAL PROPERTY VALUE ESTIMATION METHOD

(71) Applicant: Proterial, Ltd., Tokyo (JP)

(72) Inventors: Daisuke Shanai, Tokyo (JP); Takahiro Suzuki, Tokyo (JP); Tamotsu Kibe, Tokyo (JP); Takehiko Tani, Tokyo (JP)

(73) Assignee: Proterial, Ltd., Tokyo (JP)

( * ) Notice: Subject to any disclaimer, the term of this patent is extended or adjusted under 35 U.S.C. 154(b) by 559 days.

(21) Appl. No.: 18/239,390

(22) Filed: Aug. 29, 2023

(65) Prior Publication Data

US 2024/0085389 A1 Mar. 14, 2024

(30) Foreign Application Priority Data

Sep. 2, 2022 (JP) ................................ 2022-139905

(51) Int. Cl.
*G01N 33/00* (2006.01)

(52) U.S. Cl.
CPC ......... *G01N 33/00* (2013.01); *G01N 33/0003* (2024.05)

(58) Field of Classification Search
None
See application file for complete search history.

(56) References Cited

FOREIGN PATENT DOCUMENTS

JP 2007271448 A * 10/2007
JP 6627624 B 1/2020
WO WO-2022113945 A1 * 6/2022 ............ G16C 20/30

OTHER PUBLICATIONS

English machine translation of JP2007271448A (Year: 2007).*
English machine translation of Hanaoka (WO 2022113945 A1) (Year: 2022).*

* cited by examiner

*Primary Examiner* — Walter L Lindsay, Jr.
*Assistant Examiner* — Geoffrey T Evans
(74) *Attorney, Agent, or Firm* — McGinn IP Law Group, PLLC

(57) ABSTRACT

A physical property value estimation device that estimates a physical property value corresponding to a physical property required for a composite material is provided with a storage unit that stores a learned physical property regression formula corresponding to the physical property in order to calculate a physical property value corresponding to a physical property predetermined as an objective variable, by using compound data of a material that composes the composite material and feature data of the material as explanatory variables, and stores a feature amount value of the material required for calculating the feature data; a reception unit that receives compound data of the material that composes the composite material as an estimation target; and a physical property calculation unit that obtains the physical property regression formula corresponding to the physical property from the storage unit, and calculates the physical property value based on the obtained compound data by using the obtained physical property regression formula The physical property regression formula established by using the compound data and the feature data includes a feature function for calculating the feature data from the compound data and the feature amount value.

20 Claims, 7 Drawing Sheets

FIG.2

32 INPUT DATA SET

| Composition Name | Material a | Material b | Material c | Material d | Material e | Material f | Material g |
|---|---|---|---|---|---|---|---|
| Composition 1 | 50 | 30 | 20 | | 200 | | |
| Composition 2 | 50 | 30 | 20 | | | 200 | |
| Composition 3 | 50 | 30 | 20 | | | | 200 |
| Composition 4 | 30 | 40 | 20 | | 200 | | |
| Composition 5 | 30 | 40 | 20 | | | 200 | |
| Composition 6 | 30 | 40 | 20 | | | | 200 |
| Composition 7 | 50 | 30 | | 20 | 200 | | |
| Composition 8 | 50 | 30 | | 20 | | 200 | |
| Composition 9 | 50 | 30 | | 20 | | | 200 |
| Composition 10 | 30 | 40 | | 30 | 150 | | |
| Composition 11 | 30 | 40 | | 30 | 180 | | |
| Composition 12 | 30 | 40 | | 30 | 200 | | |
| Composition 13 | 30 | 40 | | 30 | | 150 | |
| Composition 14 | 30 | 40 | | 30 | | 180 | |
| Composition 15 | 30 | 40 | | 30 | | 200 | |
| Composition 16 | 30 | 40 | | 30 | | | 150 |
| Composition 17 | 30 | 40 | | 30 | | | 180 |
| Composition 18 | 30 | 40 | | 30 | | | 200 |

FIG.3

33 OUTPUT DATA SET

| Composition Name | Physical Property A | Physical Property B | Physical Property C | Physical Property D | Physical Property E |
|---|---|---|---|---|---|
| Composition 1 | 10 | 180 | 45 | 70 | 110 |
| Composition 2 | 11 | 170 | 46 | 75 | 120 |
| Composition 3 | 12 | 150 | 44 | 68 | 115 |
| Composition 4 | 9 | 175 | 47 | 65 | 105 |
| Composition 5 | 10 | 165 | 49 | 60 | 110 |
| Composition 6 | 11 | 145 | 45 | 55 | 108 |
| Composition 7 | 11 | 150 | 44 | 75 | 108 |
| Composition 8 | 12 | 140 | 45 | 73 | 110 |
| Composition 9 | 13 | 130 | 43 | 72 | 113 |
| Composition 10 | 12 | 140 | 39 | 75 | 115 |
| Composition 11 | 11 | 130 | 41 | 70 | 113 |
| Composition 12 | 9 | 120 | 44 | 68 | 110 |
| Composition 13 | 11 | 135 | 38 | 75 | 100 |
| Composition 14 | 10 | 125 | 40 | 72 | 98 |
| Composition 15 | 8 | 115 | 46 | 70 | 95 |
| Composition 16 | 10 | 200 | 37 | 70 | 105 |
| Composition 17 | 9 | 180 | 40 | 68 | 100 |
| Composition 18 | 7 | 170 | 45 | 65 | 95 |

FIG.4

34 PHYSICAL PROPERTY REGRESSION FORMULA TABLE

| Physical Property Name | Physical Property Regression Formula |
|---|---|
| Physical Property A | ya=fa (W + Feature Function 1 + Feature Function 2) ···(1) |
| Physical Property B | yb=fb (W + Feature Function 3) ···(2) |
| Physical Property C | yc=fc (W + Feature Function 1 + Feature Function 4) ···(3) |
| Physical Property D | yd=fd (W + Feature Function 4 + Feature Function 5) ···(4) |
| Physical Property E | ye=fe (W) ···(5) |

FIG.5

35 FEATURE FUNCTION TABLE

| Feature Function Name | Feature Function |
|---|---|
| Feature Function 1 | $f_1$ (W, ρ) |
| Feature Function 2 | $f_2$ (W, H) |
| Feature Function 3 | $f_3$ (W, C) |
| Feature Function 4 | $f_4$ (W, S) |
| Feature Function 5 | $f_5$ (W, **) |

FIG.6

36 FEATURE AMOUNT TABLE

| Feature Amount | Material a | Material b | Material c | Material d | Material e | Material f | Material g |
|---|---|---|---|---|---|---|---|
| Specific Gravity ($g/cm^3$) | $\rho a$ | $\rho b$ | $\rho c$ | $\rho d$ | — | — | — |
| Heat of Fusion (J/g) | Ha | Hb | Hc | Hd | — | — | — |
| Copolymer Ratio (wt%) | Ca | Cb | Cc | Cd | — | — | — |
| BET Specific Surface Area ($m^2/g$) | — | — | — | — | Se | Sf | Sg |
| ... | ... | ... | ... | ... | ... | ... | ... |

FIG.7

32a INPUT DATA SET

| Composition | Polymer 1 | Polymer 2 | Filler 3 | Filler 4 |
|---|---|---|---|---|
| TEST 1 | W1 | W2 | W3 | W4 |

FIG.8

36a FEATURE AMOUNT TABLE

| Material | Specific Gravity ($g/cm^3$) | Heat of Fusion (J/g) | Copolymer Ratio (wt%) | BET Specific Surface Area ($m^2/g$) |
|---|---|---|---|---|
| Polymer 1 | $\rho$1 | H1 | C1 | — |
| Polymer 2 | $\rho$2 | H2 | C2 | — |
| Filler 3 | $\rho$3 | — | — | S3 |
| Filler 4 | $\rho$4 | — | — | S4 |

COMPOSITE MATERIAL PHYSICAL PROPERTY VALUE ESTIMATION DEVICE, COMPOSITE MATERIAL PHYSICAL PROPERTY VALUE ESTIMATION PROGRAM, AND COMPOSITE MATERIAL PHYSICAL PROPERTY VALUE ESTIMATION METHOD

CROSS-REFERENCE TO RELATED APPLICATIONS

The present patent application claims the priority of Japanese patent application No. 2022-139905 filed on Sep. 2, 2022, and the entire contents thereof are hereby incorporated by reference.

TECHNICAL FIELD

The present invention relates to a composite material physical property value estimation device, a composite material physical property value estimation program, and a composite material physical property value estimation method.

BACKGROUND OF THE INVENTION

In recent years, a polymer composition performance estimation method is proposed to estimate the performance of a polymer composition composed of materials including multiple polymers and multiple compounding agents. (See, e.g., Patent Literature 1)

The polymer composition performance estimation method described in Patent Literature 1 includes a step of inputting data related to molecules of each material including multiple polymers and multiple compounding agents, compound ratios of materials of multiple kinds of polymer compositions, and performance data corresponding to each polymer composition to a computer, thereby making the computer structure an approximate response function; a step of inputting compound ratios of materials of a polymer composition as an estimation target, and data related to molecules of each material of the estimation target to the computer; and a step of making the computer calculates a performance of the polymer composition as the estimation target based on the approximate response function, the compounding ratio of materials of the polymer composition as the estimation target, and the data related to the molecules.

CITATION LIST

Patent Literature Patent Literature 1: JP6627624B

SUMMARY OF THE INVENTION

According to knowledge of the inventors of the present invention, data related to material features such as specific gravity, surface area, and the like of materials that compose a composite material, may influence physical properties.

The object of the present invention is to provide a composite material physical property value estimation device, a composite material physical property value estimation program, and a composite material physical property value estimation method, which allow the estimation of physical property values of a composite material with higher accuracy compared with a case where physical property values are estimated based only on compound data of materials that compose the composite material as an estimation target.

The present invention provides A physical property value estimation device that estimates a physical property value corresponding to a physical property required for a composite material, comprising:

a storage unit that stores a learned physical property regression formula corresponding to the physical property in order to calculate a physical property value corresponding to a physical property predetermined as an objective variable, by using compound data of a material that composes the composite material and feature data of the material as explanatory variables, and stores a feature amount value of the material required for calculating the feature data;

a reception unit that receives compound data of the material that composes the composite material as an estimation target; and a physical property calculation unit that obtains the physical property regression formula corresponding to the physical property from the storage unit, and calculates the physical property value based on the obtained compound data by using the obtained physical property regression formula, wherein the physical property regression formula established by using the compound data and the feature data includes a feature function for calculating the feature data from the compound data and the feature amount value.

Advantageous Effects of the Invention

According to the present invention, it is possible to perform the estimation of physical property values of a composite material with higher accuracy, compared with a case where physical property values are estimated based only on the compound data of the materials that compose the composite material as an estimation target.

BRIEF DESCRIPTION OF DRAWINGS

FIG. 2 is a table showing an example of an input data set.

FIG. 3 is a table showing an example of an output data set.

FIG. 4 is an example of a physical property regression formula table.

FIG. 5 is an example of a feature function table.

FIG. 6 is an example of a feature amount table.

FIG. 7 is a table showing an example of a simplified input data set.

FIG. 8 is an example of a simplified feature amount table.

MODE FOR CARRYING OUT THE INVENTION

Embodiment

Figure 1:
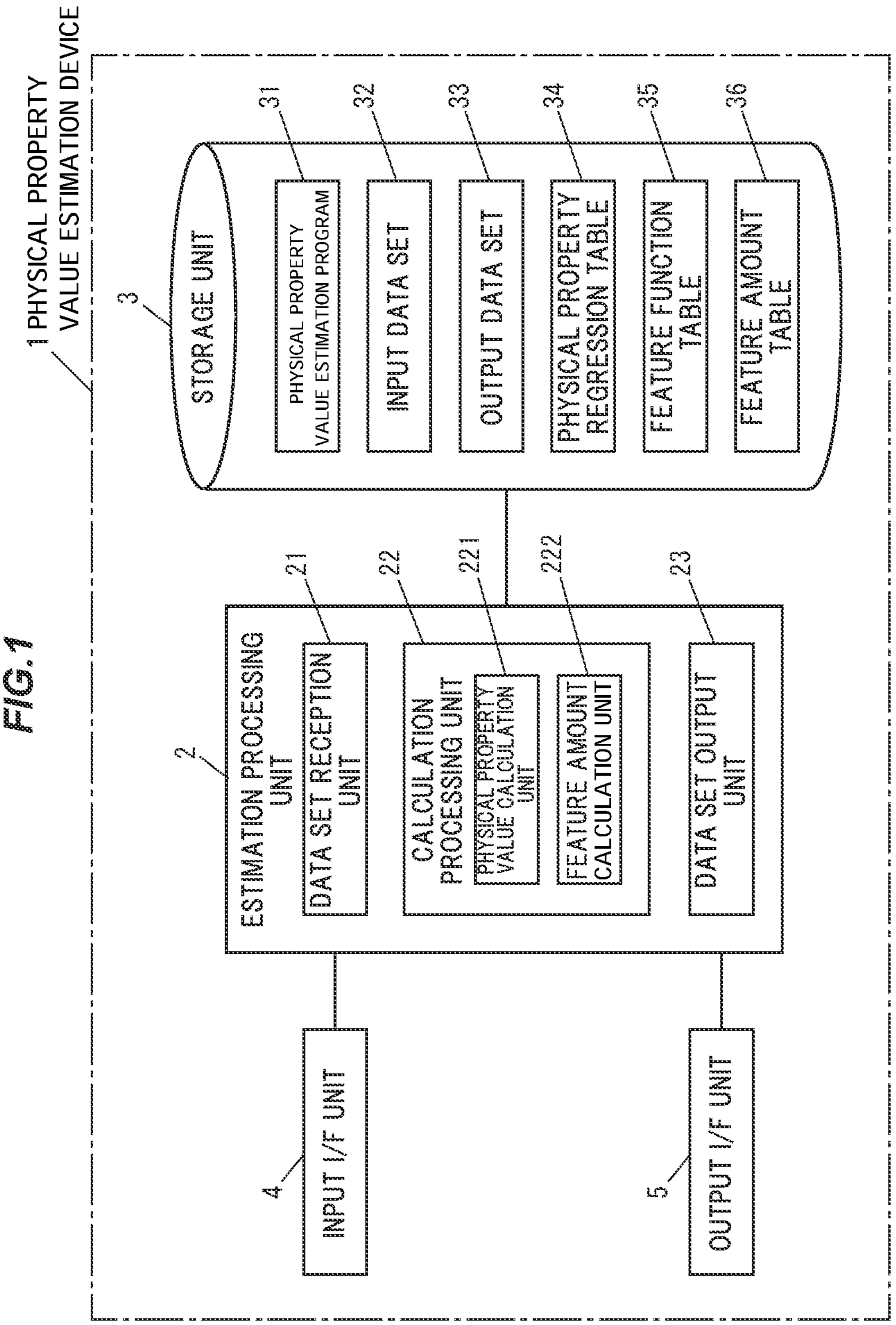
FIG. 1 is a block diagram showing a schematic configuration example of a physical property value estimation device according to an embodiment of the present invention.

FIG. 1 is a block diagram showing a schematic configuration example of a physical property value estimation device according to an embodiment of the present invention. A physical property value estimation device 1 is composed of a computer and the like, including an estimation processing unit 2, a storage unit 3, an input interface (I/F) unit 4, and an output interface (I/F) unit 5, and has a function to estimate a physical property value (or physical property values) corresponding to a required physical property (or required physical properties) for a composite material.

A composite material that the physical property value estimation device 1 is targeting is manufactured by composing component materials (hereinafter, simply referred to as "materials") that compose the composite material. The composite material can be, for example, a macromolecular (high molecular) composite material that a macromolecular material and other material(s) are composited. The macromolecular composite material can be made by using, for example, a macromolecular composition such as a polymer composition manufactured by composing multiple polymers and multiple compounding agents. The macromolecular composite material can be, for example, an electrical wire coating material, a sheet, a tube, a bond magnet, a magnet roll, and the like. The polymer composition may include one or more kinds of polymers, one or more kinds of flame retardants, and one or more kinds of antioxidants.

A "physical property" in the present specifications means a characteristic required for a composite material, for example, a mechanical physical property such as tensile elongation at break and tensile strength, or a thermal physical property such as heatproof temperature and coefficient of thermal expansion.

Explanation of estimation function of physical property values A physical property value estimation function of the physical property value estimation device 1 includes a learning function that creates an estimation model corresponding to a physical property by machine learning, and an estimation function that estimates a physical property value corresponding to the physical property by using the estimation model.

Multiple estimation models should be prepared by machine learning in order to calculate multiple physical property values corresponding to multiple physical properties predetermined as target variables by using the compound data and the feature data of materials that compose the composite material as explanatory variables. The estimation model uses a physical property regression formula made by using the compound data and the feature data of the materials in order to improve estimation accuracy. The above description is based on the learning function. The feature data of a material mentioned here is data that influences the physical property and that is figured out from the compound data and the feature amount value of the material. The feature amount value of the material is a feature that each material possesses, for example, specific gravity, surface area, and the like. A feature amount value of the material is an example of data related to the material feature.

When estimating a physical property value, the physical property value estimation device 1 receives the compound data of the materials that compose the composite material as an estimation target, and calculates the multiple physical property values corresponding to the multiple physical properties based on the received compound data by using a physical property regression formula for each physical property. The above description is based on the estimation function. Also, a physical property value corresponding to a part (one) of the predetermined multiple physical properties may be calculated. Additionally, the number of the predetermined physical properties can be one.

The estimation processing unit 2 is composed of a CPU (Central Processing Unit), a ROM (Read Only Memory), a RAM (Random Access Memory), interfaces, and the like. The estimation processing unit 2 functions as a data set reception unit 21, a calculation processing unit 22, and a data set output unit 23 by reading a physical property value estimation program 31 stored in a storage unit 3 into the RAM and executing by the CPU. The calculation processing unit 22 has a physical property value calculation unit 221 and a feature amount value calculation unit 222. The details of the respective units 21 to 23 of the estimation processing unit 2 are described later. Additionally, the respective units 21 to 23 of the estimation processing unit 2 can be configured with hardware such as an FPGA (Field Programmable Gate Array) or an ASIC (Application Specific Integrated Circuit).

The storage unit 3 is composed of a ROM, a RAM, a hard disk, and the like, and the storage unit 3 stores the physical property value estimation program 31 to execute the physical property value estimation method according to the embodiment, an input data set 32 (see FIG. 2), an output data set 33 (see FIG. 3), a physical property regression formula table 34 (see FIG. 4), a feature function table 35 (see FIG. 5), a feature amount table 36 (see FIG. 6), and the like. Also, in the present specifications, recording is used when data is written into a table, and storing is used when data is written into the storage unit. Also, the tables 34 to 36 may be stored in an external device such as a server. The input OF unit 4 is used to input a data set from a storage media connected to the physical property value estimation device 1. As the storage media, e.g., magnetic disks such as a flexible disk (FD) or a hard disk, optical disks such as a CD (Compact Disc) or DVD (Digital Versatile Disc), a USB (Universal Serial Bus) memory, and the like can be used. Additionally, the physical property value estimation program 31 can be stored and supplied in a storage media that is readable by a computer such as a CD-ROM, and can be stored in an external server such as a cloud server for being used via a network. When using the physical property value estimation program 31 stored in an external server, a data set can be input into the external server via a network such as a LAN (Local Area Network) or a WAN (Wide Area Network).

The output OF unit 5 outputs a data set to an output device connected to the physical property value estimation device 1. As an output device, for example, a display device such as a liquid crystal display or a printing device such as a printer can be used. Also, a data set can be input from and output to a terminal device connected to the physical property value estimation device 1 instead of the input OF unit 4 and the output OF unit 5. Additionally, a data set format can be, e.g., the CSV format or a table format. The data set is displayed as a table on the screen when opened in these formats.

The input data set 32 is a data set input from a storage media via the input OF unit 4 and includes the compound data of respective materials that compose multiple kinds of polymer compositions as estimation targets. The detail of the input data set 32 is described later.

The output data set 33 is a data set output to the output device via the output OF unit 5, wherein the multiple physical property values estimated by the estimation processing unit 2 for the multiple kinds of polymer compositions as estimation targets as shown in FIG. 2, are recorded. The detail of the output data set 33 is described later.

The physical property regression formula table 34 is a table wherein the physical property regression formulas are recorded corresponding to the physical property names. The feature function table 35 is a table wherein the physical property functions are recorded corresponding to the feature function names. The feature amount table 36 is a table wherein the feature amount values of the materials are recorded corresponding to the material names. The details of the table 34 to 36 are described later.

Configuration of the Input Data Set

FIG. 2 shows an example of the input data set 32 input via the input OF unit 4. The input data set 32 records the data related to the materials of the multiple kinds of polymer compositions, for each polymer composition. In concrete terms, the input data set 32 records each compound ratio (parts by mass) of a material "a" to a material "g" of material names corresponding to composition names (a composition 1 to a composition 18). The composition names are examples of identification information to identify polymer compositions. The material names are examples of identification information to identify the materials.

As a polymer composition shown in FIG. 2, an electrical wire coating material can be listed as an example. The electrical wire coating material has, e.g., polymer of the material a to the material d, and a filler of the material e to the material g. The compound ratio of a polymer in the material a to the material d is, e.g., 0 to 50 parts by mass with respect to polymer of 100 parts by mass. The compound ratio of a filler in the material e to the material g is, e.g., 0 to 200 parts by mass with respect to polymer of 100 parts by mass. The material a to the material g can be expressed by a compound amount. The compound ratio and the compound amount are examples of the compound data.

As a polymer, polyolefins such as high-density polyethylene, low-density polyethylene, ethylene acrylate copolymer, and the like, and elastomers such as chlorinated polyethylene can be listed as examples. The polymer may include ethylene copolymer.

As a compounding agent, fillers such as a flame retardant, a cross-linking agent, talc, calcium carbonate, or silica, a plasticizer, a stabilizer, and the like can be listed as examples. A flame retardant may include, e.g., either magnesium hydroxide or aluminum hydroxide, or both. Also, the kinds and the number of materials such as polymers or compounding agents that compose the polymer compositions are not limited to those mentioned above.

Configuration of Output Data Set

FIG. 3 shows an example of the output data set 33 output to the output device via the output OF unit 5. The output data set 33 includes the data related to the multiple physical properties predetermined for each polymer composition of multiple kinds. In concrete terms, physical property values corresponding to a physical property A to a physical property E of physical property names are calculated by the calculation processing unit 22 and recorded corresponding to composition names (a composition 1 to a composition 18) in the output data set 33. The physical property name is an example of identification information to identify physical properties.

Configuration of Physical Property Regression Formula Table

FIG. 4 shows an example of the physical property regression formula table 34. The physical property regression formula table 34 includes physical property regression formulas (1) to (5) corresponding to the physical property names (the physical property A to the physical property E). The physical property regression formulas (1) to (5) are established by using the compound data of the materials that compose a polymer composition, or the compound data and the feature data of the materials as explanatory variables, and configured by machine learning for calculating physical property values as target variables.

The physical property regression formulas (1) to (5) shown in FIG. 4 are as below concretely.

$$ya=fa(W\text{+feature function 1+feature function 2}) \quad (1)$$

$$yb=fb(W\text{+feature function 3}) \quad (2)$$

$$yc=fc(W\text{+feature function 1+feature function 4}) \quad (3)$$

$$yd=fd(W\text{+feature function 4+feature function 5}) \quad (4)$$

$$ye=fe(W) \quad (5)$$

Here, ya, yb, yc, yd, and ye represent physical property values corresponding to the physical property A to E respectively. Further, fa(W), fb(W), fc(W), fd(W), and fe(W) represent functions wherein the compound data "W" of the material corresponding to the physical property A to E respectively is a variable. The feature function 1 to a feature function 5 are feature function names and correspond to feature functions recorded in a feature function table 35 in FIG. 5. The feature function names are examples of identification information to identify the feature functions. The physical property regression formulas (1) to (4) are examples of the first physical property regression formula. The physical property regression formula (5) is an example of the second physical property regression formula. Also, the physical property regression formulas are not limited to the above-mentioned ones. For the physical property regression formulas, for example, more weight can be given to some elements in the function, or basic arithmetic operations other than addition can be used.

The feature data can be, for example, classified into the following groups corresponding to the material characteristics and the like.

(a) Structural Feature Data of Materials

The data here includes, e.g., a polymer volume fraction in a macromolecular composite material, a content rate of copolymer with ethylene, a denaturation amount of maleic anhydride, a volume fraction and surface area of a flame retardant in the macromolecular composite material, and the like.

(b) Thermal Feature Data of Materials

The data here includes, e.g., heat of fusion and a melt flow rate of a polymer crystal part in the macromolecular composite material, and the like.

The estimation accuracy of mechanical physical properties can be improved by using the structural feature data as feature data. Also, the estimation accuracy of thermal physical properties can be improved by using the thermal feature data as feature data. It is preferable to use the feature amount and the feature data of the material corresponding to the required physical property. For example, when the required physical property is a tensile elongation at break, a surface area of a flame retardant and the like can be used.

Configuration of Feature Function Table

FIG. 5 shows an example of the feature function table 35. The feature function table 35 includes feature functions corresponding to the feature function names (the feature function 1 to the feature function 5). In concrete terms, $f_1(W, \rho)$ corresponding to the feature function 1, $f_2(W, H)$ corresponding to the feature function 2, $f_3(W, C)$ corresponding to the feature function 3, $f_4(W, S)$ corresponding to the feature function 4, $f_5(W, )$ corresponding to the feature function 5 are recorded. Here, $F_1(W, \rho)$, $f_2(W, H)$, $f_3(W, C)$, $f_4(W, S)$, and $f_5(W, )$ are examples of the feature data. Further, "W" represents the compound data (parts by mass), "p" represents specific gravity (g/cm[3]), "H" represents heat of fusion (j/g), "C" represents copolymer ratio (Wt %), "S"

represents BET specific surface area ($m^2/g$), and "**" represents other feature amounts. The specific gravity, heat of fusion, copolymer ratio, and BET specific surface area are examples of feature amounts. Additionally, feature amounts are not limited to the above. For example, molecular weight, particle size, crystallinity and the like can be used as feature amounts.

Regarding the feature functions $f_1$ to $f_5$ shown in FIG. 5, the feature amount values corresponding to the feature function names are recorded in the feature amount table 36. In this way, inputting the feature amount values can be omitted when estimating physical property values, and the physical property values can be estimated with higher accuracy compared with a case where the physical property values are estimated without using feature data calculated based on the feature amount values.

Configuration of the Feature Amount Table

FIG. 6 shows an example of the feature amount table 36. The feature amount table 36 includes the respective feature amount values of the materials a to g: ρa to ρd, Ha to Hd, Ca to Cd, and Se to Sg, corresponding to the feature amount names respectively. In the feature amount table 36, vacant cells in which the feature amount values are not recorded mean that no feature amount values are used as the feature functions.

Configuration of the Units that Compose the Estimation Processing Unit

Next, the respective units 21 to 23 that compose the estimation processing unit 2 will be explained in detail.

The data set reception unit 21 receives the compound data of the materials that compose the polymer composition as an estimation target. In concrete terms, the data set reception unit 21 receives a data set via the input I/F unit 4 from a storage media, and stores the obtained data set as the input data set 32 in the storage unit 3. Also, the data set reception unit 21 can receive a part of the predetermined multiple physical properties (including one physical property) along with the data set. In this way, the polymer composition as an estimation target, the number of physical properties to estimate can be reduced. Additionally, the data set reception unit 21 can receive the data set including the compound data of the materials and the feature amount values of the materials. In this way, the feature functions do not need to include the feature amount values, so the capacity of the storage unit 3 can be downsized.

The calculation processing unit 22 obtains the physical property regression formulas corresponding to the physical properties from the storage unit 3, reads the compound data from the input data set 32, and calculates the physical property values based on the physical property regression formulas and the compound data by the physical property value calculation unit 221 and the feature amount calculation unit 222.

The physical property value calculation unit 221 obtains the physical property regression formulas corresponding to physical properties from the physical property regression formula table 34 regarding the predetermined multiple physical properties A to E. If the obtained physical property regression formulas include the feature functions, the physical property value calculation unit 221 obtains the feature data as calculation results after having the feature amount calculation unit 222 calculate the feature functions.

The physical property value calculation unit 221 reads the compound data of the materials from the input data set 32 corresponding to each composition, calculates respective physical property values regarding the physical properties A to E, by using the physical property regression formulas obtained from the physical property regression formula table 34, based on the calculation results of the feature functions that the feature amount calculation unit 222 has calculated and the compound data of the materials, and then records the physical property values in the corresponding cells in the output data set 33.

When the obtained physical property regression formulas do not include the feature functions, the physical property value calculation unit 221 calculates the respective physical property values of the physical properties A to E by using the obtained physical property regression formulas, based on the compound data of the materials corresponding to the compositions read from the input data set 32, and records the physical property values in the corresponding cells of the output data set 33.

The feature amount calculation unit 222 calculates the feature functions, and outputs the calculation results to the physical property value calculation unit 221. In concrete terms, the feature amount calculation unit 222 obtains the related feature amount values from the feature amount table 36, based on the feature functions obtained by the physical property value calculation unit 221, and obtain the related compound data from the compound data obtained by the physical property value calculation unit 221. The feature amount calculation unit 222 calculates the feature functions based on the obtained compound data and the feature amount values, and outputs the calculation results to the physical property value calculation unit 221.

The data set output unit 23 outputs the data set 33, wherein the physical property values are recorded in all cells, to the output device via the output OF unit 5.

Calculation Example of Feature Data

Next, an example of the feature function calculation by the feature amount calculation unit 222 is explained referring to FIG. 7 and FIG. 8.

FIG. 7 shows an example of an input data set that is the input data set 32 of FIG. 2 in a simplified form. The input data set 32*a* in FIG. 7 includes the compound data: W1, W2, W3, and W4 (parts by mass) of material names: a polymer 1, a polymer 2, a filler 3, and a filler 4 respectively according to the composition name "TEST1."

FIG. 8 shows an example of a simplified feature amount table corresponding to FIG. 7. A feature amount table 36*a* includes the specific gravity values ($g/cm^3$) ρ1 to ρ4, the heat of fusion values (J/g) H1 and H2, the copolymer ratio values (Wt %) C1 and C2 that show the copolymer content rate, and the BET specific surface area values ($m^2/g$) S3 and S4, corresponding to the material names: the polymer 1, the polymer 2, the filler 3, and the filler 4. Here, ρ1 to ρ4, H1, H2, C1, C2, S3, and S4 are examples of the feature amounts.

As an example of $f_1(W, \rho)$ of the feature function 1 in FIG. 5, the calculation of a filler volume ratio that is the ratio of filler volume ($cm^3$) to polymer volume ($cm^3$) is explained. The filler volume ratio vf_test1 is expressed by the following feature function.

$$vf\_test1=(W3/\rho 3+W4/\rho 4)/(W1/\rho 1+W2/\rho 2) \quad (6)$$

The respective W1 to W4 of the material names: the polymer 1, the polymer 2, the filler 3, and the filler 4 are obtained from the input data set 32*a* in FIG. 7, and the specific gravity values ρ1 to ρ4 of the material names: the polymer 2, the filler 3, and the filler 4 are obtained from the feature amount table 36*a* in FIG. 8, then the filler volume ratio vf_test1 is calculated based on W1 to W4, ρ1 to ρ4, and the aforementioned formula (6).

As an example of the feature function 2, $f_2$(W, H) in FIG. 5, the calculation of a synthesized heat of fusion (J/g) that is synthesized from the respective heats of fusions (J/g) of the polymers is explained. The synthesized heat of fusion, H_test1 is expressed by the following feature function.

$$H\_test1=(H1*W1+H2*W2)/(W1+W2) \quad (7)$$

The respective W1 and W2 of the materials, the polymer1 and the polymer 2 are obtained from the input data set 32*a* in FIG. 7, the respective heats of fusion H1 and H2 of the materials, the polymer1 and the polymer 2 are obtained from the feature amount table 36*a* in FIG. 8, and the synthesized heat of fusion, H_test1 is calculated based on W1, W2, H1, H2, and the aforementioned formula (7).

As an example of the feature function 3, $f_3$(W, C) in FIG. 5, the calculation of a synthesized copolymer ratio (Wt %) that is synthesized from the copolymer ratios (Wt %) of the polymers is explained. The synthesized copolymer ratio, C_test1 is expressed by the following feature function.

$$C\_test1,(C1*W1+C2*W2)/(W1+W2) \quad (8)$$

The respective W1 and W2 of the materials, the polymer 1 and the polymer 2 are obtained from the input data set 32*a* in FIG. 7, the copolymer ratios C1 and C2 of the materials, the polymer 1 and the polymer 2 are obtained from the feature amount table 36*a* in FIG. 8, and the copolymer ratio C_test1 is calculated based on W1, W2, C1, C2, and the aforementioned formula (8).

As an example of the feature function 4, $f_4$(W, S) in FIG. 5, the calculation of a filler surface area is explained. The filler surface area Sf_test1 is a product of a filler addition amount (g) multiplied by BET specific surface area ($m^2$/g), and is expressed by the following feature function.

$$Sf\_test1=S3*W3+S4*W4 \quad (9)$$

The respective W3 and W4 of the materials, the filler 3 and the filler 4 are obtained from the input data set 32*a* in FIG. 7, the BET specific surface areas S3 and S4 of the materials, the filler 3 and the filler 4 are obtained from the feature amount table 36*a* in FIG. 8, and the filler surface area Sf_test1 is calculated based on W3, W4, S3, S4, and the aforementioned formula (9).

Operation of Physical Property Value Estimation Device

Figure 9:
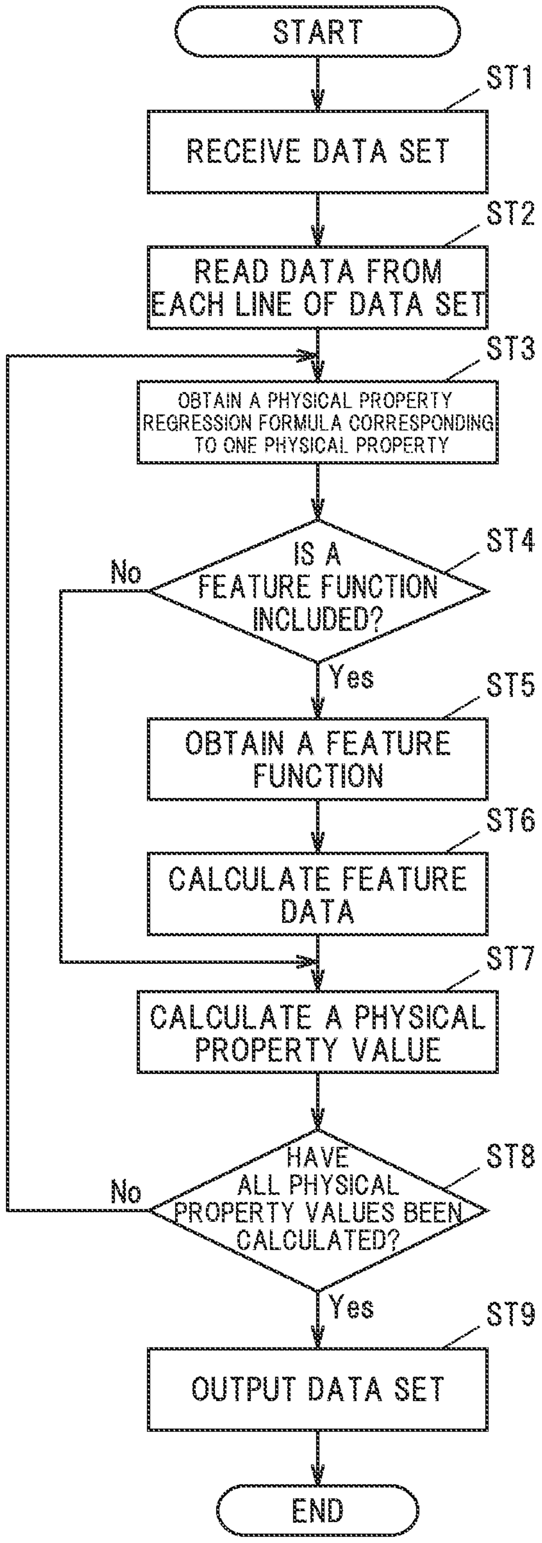
FIG. 9 is a flow chart explaining an operation example of the physical property value estimation device.

Next, an example of an operation of the physical property value estimation device 1 is explained referring to FIG. 9. FIG. 9 is a flow chart explaining an example of an operation of the physical property value estimation device 1.

The data set reception unit 21 receives a data set from the storage media via the input OF unit 4, and stores the obtained data set as the input data set 32 in the storage unit 3 (ST1).

Next, the physical property value calculation unit 221 in the calculation processing unit 22 reads data row by row from the input data set 32 (ST2). In the case shown in FIG. 2, the unit reads the respective compound data (50, 30, 20, 200) of the material names corresponding to the composition 1 in the composition name column: the material a, the material b, the material c, and the material e, . . . , the respective compound data (30, 40, 30, 100) of the material names corresponding to the composition 18: the material a, the material b, and the material d.

Then, the physical property value calculation unit 221 obtains the physical property regression formula (1) corresponding to the first physical property A among the predetermined multiple physical properties A to E from the physical property regression formula table 34. (ST3)

After that, the physical property value calculation unit 221 judges whether the obtained physical property regression formula (1) includes a feature function or not. (ST4)

In case of the physical property regression formula (1), the feature function 1 and the feature function 2 are included as the feature function names (ST3: Yes), so the physical property value calculation unit 221 obtains the feature function $f_1$(W, ρ) corresponding to the feature function 1 and the feature function $f_2$(W, H) corresponding to the feature function 2 from the feature function table 35. (ST5)

The feature amount calculation unit 222 obtains the related feature amount values ρ, H from the feature amount table 36, based on the feature function 1, $f_1$(W, ρ) and the feature function 2, $f_2$(W, H) that the physical property value calculation unit 221 has obtained, and obtains the related compound data from the compound data read in the above step ST2. Next, the feature amount calculation unit 222 respectively calculates the feature function 1, $f_1$(W, ρ) and the feature function 2, $f_2$(W, H), based on the obtained compound data and the feature amount values. (ST6) The feature amount calculation unit 222 outputs the calculation results to the physical property value calculation unit 221.

Based on the compound data read in the above step ST2 and the calculation results of the feature function 1 and the feature function 2 output from the feature amount calculation unit 222, the physical property value calculation unit 221 calculates the physical property value ya by using the physical property regression formula (1) and records the physical property value ya in the corresponding cell in the output data set 33. (ST7)

In the above step ST4, if the feature function is not included in the physical property regression formula (ST4: No), the physical property value calculation unit 221 calculates the physical property value by using the physical property regression formula (ST7) without obtaining the feature function (ST5) and calculating the feature data (ST6). For example, in the case of using the physical property regression formula (5), the physical property value calculation unit 221 calculates the physical property value ye by using the physical property regression formula (5), without obtaining the feature function (ST5) and calculating the feature data (ST6), and records the physical property value ye in the corresponding cell of the output data set 33. (ST7).

Then the physical property value calculation unit 221 judges if the calculations of the physical property values of all the physical properties have finished or not (S8). If the physical property value calculation unit 221 judges that the calculations of the physical property values of all the physical properties are not completely finished (ST8; No), it goes to the step ST3, and obtains the physical property regression formula (2) corresponding to the next physical property B from the physical property regression formula table 34. (ST3).

After that, as mentioned above, for the physical property regression formula (2), it is checked if it includes the feature function (ST4) or not, the feature function is obtained (ST5), the feature data is calculated (ST6), and the physical property value is calculated (ST7).

In the aforementioned manner, when the calculations of the physical property values in every row of the input data set 32 (ST7) is finished (ST8: Yes), the data set output unit 23 outputs the output data set 33 where the physical property values are recorded in all the cells to the output device via the output OF unit 5. (ST9) The output device outputs the contents of the output data set 33 to a display or on a sheet of paper.

Functions and Effects of the Present Embodiment

According to the present embodiment, the following functions and effects are expected.

(a) By using the physical property regression formula which includes the feature amount values of the material, inputting the feature amount values of the material (feature parameter values) such as specific gravity or surface area that are determined according to the material, can be omitted when estimating the physical property values. Especially, when estimating the multiple physical property values, the number of the feature parameter values increases according to the number of the physical property values to estimate, therefore, the effects to omit inputting them is highly advantageous.

(b) The physical property values can be estimated with higher accuracy, compared with a case where physical property values are estimated based only on the compound data of materials that compose the composite material as an estimation target. For example, according to the experiment by the inventors of the present embodiment, in a case where physical property values are estimated based only on the compound data of materials, the estimation errors of the physical property values was about 10%. However, in a case where physical property values were estimated based on the compound data and the feature data of the materials that compose the composite material as an estimation target, the estimation errors of the physical property values was about 8%.

(c) For one composite material as an estimation target, the multiple physical property values corresponding to the required multiple physical properties can be estimated all at once.

Summary of the Embodiment

Next, technical ideas understood from the above embodiment are described with reference to the reference numerals and the like used in the description of the embodiment. However, the reference numerals in the following description do not limit the constituent elements in the scope of claims to the members and the like specifically shown in the embodiment.

According to the first feature, a physical property value estimation device 1 that estimates physical a property value corresponding to a physical property required for a composite material, includes:

a storage unit 3 that stores a learned physical property regression formula corresponding to the physical property in order to calculate a physical property value corresponding to a physical property predetermined as an objective variable, by using compound data of a material that composes the composite material and feature data of the material as explanatory variables, and stores a feature amount value of the material required for calculating the feature data;

a reception unit 21 that receives compound data of the material that composes the composite material as an estimation target; and a physical property value calculation unit 221 that obtains the physical property regression formula corresponding to the physical property from the storage unit 3, and calculates the physical property value based on the obtained compound data by using the obtained physical property regression formula, wherein the physical property regression formula established by using the compound data and the feature data includes a feature function for calculating the feature data from the compound data and the feature amount value.

According to the second feature, in the physical property value estimation device 1 as described in the first feature, the storage unit 3 stores multiple physical property regression formulas learned in order to calculate multiple physical property values corresponding to multiple physical properties predetermined as objective variables, and the multiple physical property regression formulas include a first physical property regression formula established by using the compound data and the feature data as explanatory variables, and a second physical property regression formula established by using the compound data as an explanatory variable.

According to the third feature, in the physical property value estimation device 1 as described in the first feature, the feature data is structural feature data of the material.

According to the fourth feature, in the physical property value estimation device 1 as described in the third feature, the composite material is a macromolecular composite material, and the structural feature data includes at least one of a volume fraction of a polymer in the macromolecular composite material, a content rate of ethylene copolymer in the polymer, a denaturation amount of maleic acid anhydride in the polymer, a volume fraction of a flame retardant in the macromolecular composite material, and a surface area of the flame retardant.

According to the fifth feature, in the physical property value estimation device 1 as described in the first feature, wherein the feature data is thermal feature data of the material.

According to the sixth feature, in the physical property value estimation device 1 as described in the first feature, the composite material is a macromolecular composite material, and the thermal feature data includes at least one of heat of fusion of a crystal part in a polymer in the macromolecular composite material, and a melt flow rate of the crystal part.

According to a seventh feature, a physical property value estimation program 31 configured to make a computer in the physical property value estimation device 1 that estimates a physical property value corresponding to a physical property required for a composite material function as:

a reception unit that receives compound data of a material that composes the composite material as an estimation target; and a physical property calculation unit 221 that obtains a physical property regression formula corresponding to the physical property from the storage unit 3 that stores a learned physical property regression formula corresponding to the physical property in order to calculate the physical property value corresponding to the physical property predetermined as an objective variable, by using compound data of the material that composes the composite material and feature data of the material as explanatory variables, and stores the feature amount value of the material required for calculating the feature data, and calculates the physical property value based on the obtained compound data by using the obtained physical property regression formula, wherein the physical property regression formula established by using the compound data and the feature data includes a feature function for calculating the feature data from the compound data and the feature amount value.

According to the eighth feature, a physical property value estimation method for estimating a physical property value corresponding to a physical property required for a composite material, includes:

a reception step of receiving compound data of a material that composes the composite material as an estimation target; and a physical property calculation step of obtaining a physical property regression formula corresponding to the physical property from the storage unit 3 that stores a learned physical property regression formula corresponding to the physical property in order to calculate the physical property value corresponding to the physical property predetermined as an objective variable, by using compound data of the material that composes the composite material and feature data of the material as explanatory variables, and stores feature values of the materials required for calculating the feature data, and calculating the physical property value based on the obtained compound data by using the obtained physical property regression formula, wherein the physical property regression formula established by using the compound data and the feature data includes a feature function for calculating the feature data from the compound data and the feature amount value.

The above is all for the explanation of the embodiment of the present invention, but the embodiment of the present invention is not limited to the aforementioned one, but various modifications and implementations are possible.

Additionally, a part of the constituent elements of the embodiment can be omitted or modified. In the flow of the embodiment, a step(s) can be added, removed, modified, or swapped.

The invention claimed is:

1. A physical property value estimation device that estimates a physical property value corresponding to a physical property required for a composite material, comprising:

a storage unit that stores a learned physical property regression formula corresponding to the physical property in order to calculate a physical property value corresponding to a physical property predetermined as an objective variable, by using compound data of a material that composes the composite material and feature data of the material as explanatory variables, and stores a feature amount value of the material required for calculating the feature data;

a reception unit that receives compound data of the material that composes the composite material as an estimation target; and a physical property calculation unit that obtains the physical property regression formula corresponding to the physical property from the storage unit, and calculates the physical property value based on the obtained compound data by using the obtained physical property regression formula, wherein the physical property regression formula established by using the compound data and the feature data includes a feature function for calculating the feature data from the compound data and the feature amount value, and wherein the composite material comprises a polymer composition.

2. The physical property value estimation device, according to claim 1, wherein the storage unit stores multiple physical property regression formulas learned in order to calculate multiple physical property values corresponding to multiple physical properties predetermined as objective variables, and the multiple physical property regression formulas include a first physical property regression formula established by using the compound data and the feature data as explanatory variables, and the second physical property regression formula established by using the compound data as an explanatory variable.

3. The physical property value estimation device, according to claim 1, wherein the feature data is structural feature data of the material.

4. The physical property value estimation device, according to claim 3, wherein the composite material is a macromolecular composite material, and the structural feature data includes at least one of a volume fraction of a polymer in the macromolecular composite material, a content rate of ethylene copolymer in the polymer, a denaturation amount of maleic acid anhydride in the polymer, a volume fraction of a flame retardant in the macromolecular composite material, and a surface area of the flame retardant.

5. The physical property value estimation device, according to claim 1, wherein the feature data is thermal feature data of the material.

6. The physical property value estimation device, according to claim 5, wherein the composite material is a macromolecular composite material, and the thermal feature data includes at least one of heat of fusion of a crystal part in a polymer in the macromolecular composite material, and a melt flow rate of the crystal part.

7. The physical property value estimation device according to claim 1, wherein the polymer composition is a macromolecular composite material comprising at least one polymer and at least one compounding agent.

8. The physical property value estimation device according to claim 7, wherein the at least one polymer comprises at least one of a polyolefin, an ethylene acrylate copolymer, and a chlorinated polyethylene, and the at least one compounding agent comprises at least one of a flame retardant, a cross-linking agent, a plasticizer, and a stabilizer.

9. The physical property value estimation device according to claim 7, wherein the flame retardant comprises at least one of magnesium hydroxide and aluminum hydroxide.

10. The physical property value estimation device according to claim 1, wherein the feature amount value comprises at least one of a specific gravity of the material, a BET specific surface area of the material, a heat of fusion of a crystal part of the material, a melt flow rate of the crystal part, a copolymer ratio of the material, and a denaturation amount of maleic acid anhydride in the material.

11. The physical property value estimation device according to claim 1, wherein the physical property comprises at least one of a tensile elongation at break, a tensile strength, a heatproof temperature, and a coefficient of thermal expansion of the polymer composition.

12. The physical property value estimation device according to claim 1, wherein the storage unit further stores a feature function table recording a plurality of feature functions corresponding to respective feature function names, and the physical property regression formula references the feature functions by the respective feature function names.

13. The physical property value estimation device according to claim 12, wherein the storage unit further stores a feature amount table recording feature amount values of each material corresponding to material names, and the physical property calculation unit obtains feature amount values from the feature amount table based on the feature functions obtained from the feature function table.

14. The physical property value estimation device according to claim 1, wherein the polymer composition is an electrical wire coating material, a sheet, a tube, a bond magnet, or a magnet roll.

15. A physical property value estimation program configured to make a computer in a physical property value estimation device that estimates a physical property value corresponding to a physical property required for a composite material function as:

a reception unit that receives compound data of the material that composes the composite material as an estimation target; and a physical property calculation unit that obtains a physical property regression formula corresponding to the physical property from the storage unit that stores a learned physical property regression formula corresponding to the physical property in order to calculate the physical property value corresponding to the physical property predetermined as an objective variable, by using compound data of the material that composes the composite material and feature data of the materials as explanatory variables, and stores a feature amount value of the material required for calculating the feature data, and calculates the physical property value based on the obtained compound data by using the obtained physical property regression formula, wherein the physical property regression formula established by using the compound data and the feature data includes a feature function for calculating the feature data from the compound data and the feature amount value, wherein the composite material function comprises a polymer composition function.

16. The physical property value estimation program according to claim 15, wherein the polymer composition is a macromolecular composite material comprising at least one polymer and at least one compounding agent, and wherein the feature amount value comprises at least one of a specific gravity of the material, a BET specific surface area of the material, a heat of fusion of a crystal part of the material, a melt flow rate of the crystal part, and a copolymer ratio of the material.

17. A physical property value estimation method for estimating a physical property value corresponding to a physical property required for a composite material, comprising:

a reception step of receiving compound data of a material that composes the composite material as an estimation target; and a physical property calculation step of obtaining a physical property regression formula corresponding to the physical property from the storage unit that stores a learned physical property regression formula corresponding to the physical property in order to calculate the physical property value corresponding to the physical property predetermined as an objective variable, by using compound data of a material that composes the composite material and feature data of respective materials as explanatory variables, and stores a feature amount value of the material required for calculating the feature data, and calculating the physical property value based on the obtained compound data by using the obtained physical property regression formula, wherein the physical property regression formula established by using the compound data and the feature data includes a feature function for calculating the feature data from the compound data and the feature amount value, and wherein the composite material comprises a polymer composition.

18. The physical property value estimation method according to claim 17, wherein the polymer composition is a macromolecular composite material comprising at least one polymer and at least one compounding agent, and wherein the feature amount value comprises at least one of a specific gravity of the material, a BET specific surface area of the material, a heat of fusion of a crystal part of the material, a melt flow rate of the crystal part, and a copolymer ratio of the material.

19. The physical property value estimation method according to claim 17, further comprising: a feature data calculation step of, when the physical property regression formula includes a feature function, obtaining the feature function from a feature function table stored in the storage unit, obtaining a feature amount value of the material from a feature amount table stored in the storage unit, and calculating the feature data based on the compound data and the feature amount value; wherein the physical property calculation step calculates the physical property value based on the compound data and the calculated feature data.

20. The physical property value estimation method according to claim 17, further comprising: an output step of outputting an output data set recording physical property values corresponding to a plurality of physical properties for each of a plurality of polymer compositions, wherein the physical property calculation step calculates the physical property values for each of the plurality of physical properties by iterating through respective physical property regression formulas stored in the storage unit.

* * * * *